United States Patent [19]

Nudelman et al.

[11] Patent Number: 5,240,833
[45] Date of Patent: Aug. 31, 1993

[54] METHOD FOR THE PRODUCTION OF MONOCLONAL ANTIBODIES DIRECTED TO TUMOR-ASSOCIATED GANGLIOSIDES AND FUCOGANGLIOSIDES

[75] Inventors: Edward Nudelman; Anil Singhal; Henrik Clausen; Sen-itiroh Hakomori, all of Seattle, Wash.

[73] Assignee: The Biomembrane Institute, Seattle, Wash.

[21] Appl. No.: 787,778

[22] Filed: Nov. 6, 1991

Related U.S. Application Data

[63] Continuation of Ser. No. 387,683, Jul. 31, 1989, abandoned, which is a continuation of Ser. No. 302,890, Jan. 30, 1989, abandoned.

[51] Int. Cl.$^5$ .................... C12P 21/08; C12N 15/02; C12N 5/12; C07K 15/28
[52] U.S. Cl. .................... 435/70.21; 435/172.2; 435/240.27; 530/388.25; 530/388.8
[58] Field of Search .................. 435/70.21, 172.2; 530/388.25, 388.8

[56] References Cited

U.S. PATENT DOCUMENTS 4,876,199  10/1989  Kakomori ........................ 530/387

OTHER PUBLICATIONS

Riboni, et al., J. of Biological Chemistry, vol. 261 (18):8514-8519, Jun. 25, 1986.
Clausen, H. et al., J. of Immunology, vol. 136(1):326-330, Jan. 1, 1986.
Portoukalian et al., Biochem Biophys Res. Commun., vol. 85(3):916-920, Dec. 14, 1978.
Finne, J., et al., J. Biological Chemistry, vol. 264(10):5720-5735, Apr. 5, 1989.
Krivan, H. C., et al., PNAS, vol. 85:6157-6161, Aug. 1988.

*Primary Examiner*—David L. Lacey
*Assistant Examiner*—Susan L. Futrovsky
*Attorney, Agent, or Firm*—Sughrue, Mion, Zinn, Macpeak & Seas

[57] ABSTRACT

A method of producing monoclonal antibodies that bind to tumor-associated gangliosides, the method comprising: (1) immunizing a host with tumor cells; (2) boosting the host with a suspension comprising a mixture of tumor cell membrane and at least one purified lactonized tumor-associated ganglioside; (3) boosting the host with an immunogen comprising a lactone of a tumor associated ganglioside adsorbed on or incorporated into a carrier; (4) fusing immunized cells from the host with myeloma cells to form hybridoma cells: (5) selecting hybridoma cells that produce antibody that binds to the ganglioside of step (3); (6) culturing the selected hybridoma cells; and (7) recovering the antibody. Hybridomas and monoclonal antibodies produced by the above-described method. A passive immunization method for treatment of tumors containing gangliosides comprising administering to a subject: (A) a pharmaceutically effective amount of an antibody produced by the above described method. A method for detecting tumors containing gangliosides comprising: (A) contacting a test sample with an antibody produced by the above described method; and (B) assaying for the specific binding of the antibody to antigen in the test sample.

2 Claims, 4 Drawing Sheets

1 2 3 4 5 6 7 8 9 10 11
NKH1

FIG. 3B

1 2 3 4 5 6 7 8 9 10 11
NKH2

FIG. 3C 1 2 3 4 5 6 7 8 9 10 11
NKH3

FIG. 3D 1 2 3 4 5 6 7 8 9 10 11
anti-Le$^a$

METHOD FOR THE PRODUCTION OF MONOCLONAL ANTIBODIES DIRECTED TO TUMOR-ASSOCIATED GANGLIOSIDES AND FUCOGANGLIOSIDES

Portions of the invention(s) disclosed herein were supported in part by a grant from the National Cancer Institute, Department of Health and Human Services.

This is a Continuation of application No. 07/387,683 filed 31 Jul. 1989, abandoned, which is a Continuation of application No. 07/302,890 filed 30 Jan. 1989, abandoned.

FIELD OF THE INVENTION

The present invention relates to an improved method for the production of monoclonal antibodies to tumor-associated gangliosides and to the hybridomas and monoclonal antibodies produced therefrom. More particularly, the present invention relates to new methods for the preparation of monoclonal antibodies directed to tumor-associated gangliosides which use in the immunization steps a booster of purified ganglioside lactones. The present invention also relates to the novel hybridomas produced by the improved method and to the novel monoclonal antibodies produced by the hybridomas. The monoclonal antibodies are useful in the detection and treatment of tumors containing gangliosides.

BACKGROUND OF THE INVENTION

Cells are surrounded by plasma membranes. Plasma membranes contain components called glycosphingolipids inserted therein which aide in the formation of the characteristic surface structure of the cells. Each type of cell is characterized by a specific profile of the glycosphingolipid components, including those components known as gangliosides, located in its plasma membrane Gangliosides contain a particular type of acidic carbohydrate known as sialic acid. Further, many specific types of cells, including tumor cells. are characterized by the presence of a particular type of ganglioside located in their plasma membranes.

In recent years, a number of monoclonal antibodies have been established after immunization with human tumor cells or tissues. These monoclonal antibodies were selected by their positive reactivity to tumor cells and negative reactivity to normal cells or tissues. Many of the monoclonal antibodies selected by preferential reactivity to melanomas, neuroblastomas and adenocarcinomas have been identified as being directed to gangliosides. Some of these anti-ganglioside antibodies with specific isotopes (particularly IgG$_3$ and IgG$_{2a}$) and which show strong reactivity to gangliosides, have been found to suppress tumor growth in vivo. For example, melanomas of some patients have been found to regress following a large dose administration of a specific anti-GD$_3$ ganglioside antibody (Houghton, A.N. et al, *Proc. Natl. Acad. Sci. USA.* 82:1242-1246 (1985)). Further, recently it has been demonstrated that GM$_2$ absorbed on BCG bacteria showed a detectable immune response. Thus, it has been asserted that GM$_2$ could be a useful vaccine for human melanomas (Livingston. P.O. et al. *Proc. Natl. Acad. Sci. USA.* 84:2911-2915 (1987). Hence, gangliosides are important antigens and immunogens of tumor tissues and cells (Hakomori. S.. *Annu. Rev. Immunol.,* 2:103-126 (1984): Hakomori, S., In *Handbook of Lipid Research,* Volume 3, *Sphingolipid Biochemistry,* Kanfer, J.N. et al Eds., Plenum, New York, pages 1-165 (1983); and Hakomori, S., *Sci. Amer.,* 254:44-53 (1986)).

However, although gangliosides are important cell type-specific markers, they are poor immunogens in eliciting humoral or cellular immune responses.

A small portion of gangliosides are present in tumor cells and tissues in the form of a lactone thereof. For example, less than 0.1% of the particular ganglioside, designated GM$_3$, present in melanoma cells has been identified as a lactone thereof. Ganglioside lactones are defined as the inner ester between the carboxyl group of the sialic acid and the primary or secondary hydroxyl group of the sugar residues within the same molecule.

While galactoside lactones have been detected and are believed to be naturally occurring plasma membrane components, their quantity is extremely low and thus their natural occurrence has been disputed (Nores, G.A. et al, *J. Immunol.,* 139:3171-3176 (1987) and Riboni, L., *J. Biol. Chem.,* 261:8514-8519 (1986)).

Despite the question about their natural occurrence, it has been demonstrated that ganglioside lactones are strong immunogens, which can cause a much greater immune response than native gangliosides (Nores, G.A. et al. *J. Immunol.,* 139:3171-3176 (1987)). Further. Nores et al found that the antibodies produced using ganglioside lactones as immunogens are of the IgG$_3$ isotype.

In the present invention, it has been found that the use of tumor cells and tumor cell membranes followed by a booster with purified ganglioside lactones in the immunization step of producing hybridomas provides new hybridomas that produce monoclonal antibodies directed to a variety of tumor-associated gangliosides, including human cancer-associated fucogangliosides. Further, while some of the new antibodies show similar binding specificity to known antibodies, their isotypes are different. Therefore their pharmacodynamic activity is also expected to be different. Also many of the new antibodies have unique cross-reactivity.

SUMMARY OF THE INVENTION

Accordingly, an object of the present invention is to provide an improved method for the production of antibodies to tumor-associated gangliosides, and especially tumor-associated fucogangliosides.

It is also an object of the present invention to provide novel hybridomas that produce monoclonal antibodies to particular tumor-associated antigens.

It is further an object of the present invention to provide novel monoclonal antibodies to particular tumor-associated antigens.

Another object of the present invention is to provide a passive immunization method for treating tumors containing gangliosides.

Still another object of the present invention is to provide a method for detecting tumors containing gangliosides.

These and other objects of the present invention, which will be apparent from the detailed description of the invention provided hereinafter, have been met by the following embodiments.

In one embodiment, the present invention relates to a method of producing monoclonal antibodies that bind to tumor-associated gangliosides, the method comprising:

(1) immunizing a host with tumor cells;

(2) boosting said host with a suspension comprising a mixture of tumor cell membrane and at least one purified lactonized tumor-associated ganglioside;

(3) boosting said host with an immunogen comprising a lactone of a tumor associated ganglioside adsorbed on or incorporated into a carrier;

(4) fusing immunized cells from said host with myeloma cells to form hybridoma cells:

(5) selecting hybridoma cells that produce antibody that binds to said ganglioside of step (3):

(6) culturing said selected hybridoma cells: and (7) recovering said antibody.

The present invention also provides a hybridoma cell line that produces a monoclonal antibody having the following identifying characteristics:

(1) Isotype is IgM:
(2) Binds to:
(a) sialyl Le$^x$, and
(b) sialyl difucosyl Le$^x$;

A hybridoma cell line that secretes a monoclonal antibody having the following identifying characteristics:

(1) Isotype is IgG$_1$;
(2) Binds to sialyl 2→3 Le$^a$;

A hybridoma cell line that secretes a monoclonal antibody having the following identifying characteristics:

(1) Isotype is IgM:
(2) Binds to:
(a) sialyl 2→3 Le$^a$, and
(b) Le$^a$,
(c) pentaosyl- and hexaosylceramide carrying the Le$^a$ epitope,
(d) Le$^a$/Le$^x$ hybrid, and
(e) bivalent Le$^a$ on lactoisooctaosylceramide: and A hybridoma cell line that produces a monoclonal antibody having the following identifying characteristics:

(1) Isotype is IgG$_1$;
(2) Binds to:
(a) sialyl 2→3 Le$^a$, and
(b) sialyl 2→3 type 1 chain paragloboside, when tested with auxiliary lipids or by TLC immunostaining with plastic-coated plate.

In a further embodiment, the present invention provides the monoclonal antibodies produced by the above-identified hybridomas.

In an even further embodiment, the present invention provides a passive immunization method for treatment of tumors containing gangliosides comprising administering to a subject: a pharmaceutically effective amount of an antibody produced by a method comprising:

(1) immunizing a host with tumor cells:
(2) boosting said host with a suspension comprising a mixture of tumor cell membrane and at least one purified lactonized tumor-associated ganglioside;
(3) boosting said host with an immunogen comprising a lactone of a tumor associated ganglioside adsorbed on or incorporated into a carrier;
(4) fusing immunized cells from said host with myeloma cells to form hybridoma cells;
(5) selecting hybridoma cells that produce antibody that binds to said ganglioside of step (3):
(6) culturing said selected hybridoma cells; and
(7) recovering said antibody.

In an even further embodiment, the present invention provides a method for detecting tumors containing gangliosides comprising:

(A) contacting a test sample with an antibody produced by a method comprising:

(1) immunizing a host with tumor cells;
(2) boosting said host with a suspension comprising a mixture of tumor cell membrane and at least one purified lactonized tumor-associated ganglioside;
(3) boosting said host with an immunogen comprising a lactone of a tumor associated ganglioside adsorbed on or incorporated into a carrier;
(4) fusing immunized cells from said host with myeloma cells to form hybridoma cells;
(5) selecting hybridoma cells that produce antibody that binds to said ganglioside of step (3);
(6) culturing said selected hybridoma cells; and
(7) recovering said antibody: and (B) Assaying for specific binding of said antibody to antigen in said test sample.

BRIEF DESCRIPTION OF THE FIGURES

FIG. 1 is a graph showing the results of a radioimmune assay using the monoclonal antibody SNH3 according to the present invention. The ordinate represents the activity of protein A binding to primary and secondary antibody, in counts per minute. The abscissa represents the antigen dilution wherein the first well (denoted as 1) contained 100 ng antigen, the second well (denoted as 2) contained 50 ng antigen. etc. The open circles represent sialyl difucosyl Le$^x$ (structure 2, Table I: VI$^3$NeuAcV$^3$FucIII$^3$FucNLc$_6$) isolated from tumor. The open triangles represent the same antigen, but synthesized enzymatically from sialyl 2→3 norhexaosylceramide. The closed, upside down triangles represent sialyl Le$^x$ hexasaccharide ceramide isolated from tumor (structure 1, Table I; IV$^3$NeuAcIII$^3$FucnLc$_4$) The open, upside down triangles represent sialyl 2→3 norhexaosylceramide. The closed circles represent GM$_3$, 2→3 sialylparagloboside (SPG) IV$^3$NeuAcnLc$_4$), 2→6 SPG (VI$^6$ NeuAcnLc$_4$), sialyl 2→3 Le$^a$ (structure 3, Table I IV$^2$NeuAcIII$^4$FucLc$_4$), and sialyl 2→6 norhexaosylceramide (VI$^6$NeuAcnLc$_6$)

FIG. 2 is graphs showing the reactivity of antibodies NKH1 (FIG. 2A), NKH2 (FIG. 2B), NKH3 (FIG: 2C). NKH4 (FIG. 2D) and CF4C4 (a known anti-Le$^a$ antibody: FIG. 2E) by solid-phase radioimmunoassay. The ordinate represents the activity of protein A binding to secondary antibody which reacts with primary antibody bound to the antigen. The abscissa represents the antigen dilution as described for FIG. 1 above. The open triangles represent sialyl 2→3 Le$^a$ purified from tumor (structure 3, Table I; IV$^3$NeuAcIII$^4$FucLc$_4$). The open, upside down triangles represent the same antigen, but isolated from meconium (also contains disialyl Le$^a$). The closed squares represent sialylparagloboside (SPG) type 1 chain. The closed triangles represent Le$^a$ (structure 5, Table I; III$^4$FucLc$_4$). The closed, upside down triangles represents Le$^a$/Le$^x$ hybrid (structure 7, Table I). The closed circles represent bivalent Le$^a$ on lactoisooctaosylceramide (iso-Le$^a$) (structure 8, Table I). The open squares represent synthetic sialyl 2→3 paragloboside.

FIG. 3 shows immunostaining patterns of various glycolipid samples with antibodies NKH1 (FIG. 3A), NKH2 (FIG. 3B). NKH3 (FIG. 3C) and an anti-Le$^a$ antibody (FIG. 3D). Lane 1: monosialoganglioside fraction of meconium; lane 2: monosialoganglioside fraction of meconium treated with sodium methoxide (in order to determine possible presence of gangliosides containing O-acetyl group): lane 3: upper neutral glycolipids of O erythrocytes: lane 4: monosialoganglioside fraction from human colonic cancer cell line Colo 205; lane 5: Le$^a$-active ceramide pentasaccharide (III$^4$FucLc$_4$Cer; structure 5, Table I): lane 6: sialyl 2→3 paragloboside type 1 chain isolated from meconium (structure 4, Table I); lane 7: sialyl 2→3 paragloboside type 1 chain synthesized from CMP-sialic acid and Lc$_4$Cer (type 1 chain paragloboside) (structure 4, Table I); lane 8: sialyl 2→3 Le$^a$ (IV$^3$NeuAcIII$^4$FucLc$_4$Cer; structure 3, Table I); lane 9: Le$^a$ on Le$^x$ determinant (IV$^3$Gal$\beta$1→3-[Fuc$\alpha$1→4]GlcNAc-III$^3$FucnLc$_4$Cer; structure 7, Table I); lane 10: Le$^a$ on branched lactoisooctaosylceramide (V$^3$FucIV$^6$Gal$\beta$1→3-[Fuc$\alpha$1→3]GlcNAcnLc$_6$Cer; structure 8, Table I.

DETAILED DESCRIPTION OF THE INVENTION

According to the present invention there is provided a novel method of producing monoclonal antibodies directed to tumor-associated gangliosides. An important aspect of the method is that the immunization of the host includes a booster step using a lactone of a tumor associated ganglioside.

The method comprises:

(1) immunizing a host with tumor cells:

(2) boosting said host with a suspension comprising a mixture of tumor cell membrane and at least one purified lactonized tumor-associated ganglioside;

(3) boosting said host with an immunogen comprising a lactone of a tumor associated ganglioside adsorbed on or incorporated into a carrier;

(4) fusing immunized cells from said host with myeloma cells to form hybridoma cells;

(5) selecting hybridoma cells that produce antibody that binds to said ganglioside of step (3);

(6) culturing said selected hybridoma cells; and (7) recovering said antibody.

The particular tumor cells and tumor cell membrane used in steps (1) and (2), respectively, of the method are not particularly limited and any of those conventionally used in the production of hybridomas that produce antibodies to tumor cell antigens can be used (Fukushi et al. *J. Biol. Chem.* 259: 4672–4680 (1984) and *J. Biol. Chem.* 259:10511–10517 (1984)).

Specific examples include colonic cancer cells (e.g. SW948 and colo205) and human lung carcinoma cells (e.g. PC9).

Immunization with the tumor cells is conducted according to conventional methods.

The membrane fraction used in step (2) is prepared in a conventional manner (Fukushi, et al *J. Biol. Chem.* 259:4572–4680 (1984) and *J. Biol. Chem.* 259:10511–10517 (1984)).

A mixture of a tumor cell membrane and at least one purified lactonized tumor-associated ganglioside is used for immunization in step (2). The mixture can be prepared by adding purified lactonized tumor-associated ganglioside to a membrane fraction and incubating at pH 6.0–6.5 (at this pH. lactones are stable). Alternatively the mixture can be prepared by treating the mixture by known methods to lactonize the tumor cell membrane gangliosides and the purified ganglioside.

For example, the membrane fraction is prepared, suspended in 5% acetic acid, mixed with purified gangliosides and then lyophilized. This procedure induces lactonization and enrichment of membrane gangliosides.

The lyophilized material is suspended in PBS and injected intravenously, according to well known methods.

The particular tumor-associated ganglioside employed in steps (2) and (3) of the present invention is not critical thereto. Examples of such tumor-associated gangliosides include GD$_3$ found in melanomas (Pukel. C.S. et al, *J. Exp. Med.*, 155:1133–1147 (1982) and Nudelman, E. et al. *J. Biol. Chem.*, 257:12752–12756 (1982)): GD$_2$ found in melanomas and neuroectodermal tumors such as neuroblastomas (Cahan. L. et al., *Proc. Natl. Acad. Sci. USA,* 79:7629–7633 (1982)): sialyl Le$^a$ found in gastrointestinal and pancreatic cancers (Magnani. J. L. et al *J. Biol. Chem.*, 257:14365–14369 (1982)); sialyl Le$^x$ found in colorectal, gastrointestinal and lung adenocarcinomas (Fukushima. K. et al. *Cancer Res.*, 44:5279–5285 (1984)): sialyl difucosyl Le$^x$ found in colorectal, gastrointestinal and lung adenocarcinomas (Fukushi, Y. et al. *J. Biol. Chem.*, 259:10511–10517 (1984)); GM$_3$ found in melanomas (Taniguchi, M., *Gann,* 75:418–426 (1984): Hirabayashi, Y. et al.. *J. Biol. Chem.*, 260:13328–13333 (1985): Nores. G. et al. *J. Immunol.*, 139:3171–3176 (1987): 6C ganglioside found in colorectal carcinomas (Hakomori, S. et al., *Biochem. Biophys. Res. Commun.*, 113:791–798 (1983): G2 ganglioside found in myelogeneous leukemia cells (Fukuda. Y. et al.. *J. Biol. Chem.*, 260:1060–1082 (1985): disialosyl Le$^a$ found in colorectal cancers (Nudelman, E. et al.. *J. Biol. Chem.*, 261:5487–5495 (1986); monosialyl type 1 chain found in colorectal carcinomas and teratocarcinomas (Nilsson. 0. et al, *FEBS Letters,* 182:398–402 (1985): Fakuda, M.,N. et al, *J. Biol. Chem.*, 261:5145–5153 (1986): disialosyl type 1 chain found in colorectal cancers (Fukushi, Y. et al. *Biochem.*, 25:2859–2866 (1986); and fucosyl GM$_1$ found in small cell lung carcinomas (Nilsson. O. et al., *Glycoconjugate J.*, 143–49 (1984)).

Lactones of the gangliosides for use in step (3) of the method can be prepared by known methods (Nores, G. A. et al, *J. Immunol.* 139:3171–3176 (1987)).

For example, the lactones can be prepared by dissolving any ganglioside in glacial acetic acid and allowing the solution to stand for at least 48 hours, followed by lyophilization of the acetic acid. Formation of the ganglioside lactones can be monitored by thin layer chromatography, using high performance thin layer chromatography plates obtained from J. T. Baker Chemical Co. (Phillipsburg. N.J.) and chloroform:methanol:water (50:40:10 (v/v/v)) containing 0.05% (w/v) CaCl$_2$ as a solvent since ganglioside lactones show a distinctively higher mobility than native gangliosides on thin layer chromatography. The above solvent composition is not critical and any well known solvent which can separate gangliosides from the lactones thereof can be employed, for example, as described in Nores, G. A. et al., *J. Immunol.,* 139:3171–3176 (1987).

Alternatively, and more efficiently, ganglioside lactones can be prepared by dissolving any ganglioside in chloroform:methanol:12N HCl (10:35:4.5 (v/v/v)) and allowing the solution to stand for about one day. The resulting solution is then chromatographed using DEAE-SEPHADEX in chloroform:methanol:water (0.1:1:1 (v/v/v)). Two main components and several minor components, the structures of the latter remain to be elucidated, are resolvable in this system. The resulting ganglioside lactones can be purified by HPLC on IATROBEADS 6RS8010 in isopropanol:hexane:water (55:25:20 (v/v/v)) with gradient elution being carried out as described by Watanabe, K. et al., *J. Lipid Res.*, 22:1020–1024 (1981). The structure of the purified ganglioside lactones can be verified by direct probe fast atom bombardment mass spectrometry as described in Riboni, L., *J. Biol. Chem.*, 261:8514–8519 (1986).

Ganglioside lactones can also be prepared by treatment with carbodiimide (Sonnino. S. et al, *Glycoconjugate J.*, 2:343–354 (1985)).

The purified lactonized ganglioside is administered to the host intravenously along with a suitable carrier.

The particular carrier to be used along with the lactone of the tumor-associated ganglioside is not critical to the present invention. Examples of such acceptable carriers include acid-treated *Salmonella minnesotae*, reconstituted viral membranes such as Newcastle's disease virus membranes and any reconstituted cell membranes incubated with octylglucose followed by dialysis.

The particular host being immunized for eventual production of hybridomas is not critical to the present invention. Examples of suitable hosts include mice, rabbits, rats and goats.

As used herein "immunized cells" refers to the sensitized spleen cells of the immunized host, e.g.. those of mice such as Balb/c mice.

The particular myeloma cells employed in the present invention are not critical thereto and can be any well known myeloma cell useful for preparing hybridomas of mouse, rat, rabbit, goat and human origin. Examples of such myeloma cells include HAT sensitive mice myeloma cells such as NS/1 cells and Sp-2 cells.

The amount of tumor cells, membrane/ganglioside mixture and lactone of the tumor-associated ganglioside to be administered in the present invention will vary depending upon the age, weight, sex and species of the animal being immunized and can readily be determined by the skilled artisan. By way of example, one suitable immunogenic effective amount of the lactone is about 2.0 to 5.0 $\mu$g. absorbed on about 20 to 100 $\mu$g of carrier per one injection.

Immunizing the animals, e.g.. mice, with the ganglioside lactones of the present invention, isolating the immunized cells, fusing the immunized cells with, e.g., mouse myeloma cells, and culturing the resulting fused cells under conditions which allow for growth of hybridomas, are all conducted by methods well known and readily determined in the art (Young, W. W. et al, *J. Exp. Med.*, 150:1008–1019 (1979) and Fukushi, Y. et al, *J. Biol. Chem.*, 259:4681–4685 (1984)).

The resulting hybridomas are then screened so as to isolate those which produce monoclonal antibodies having binding specificity to the ganglioside used to prepare the lactone in step (3), in for example a solid-phase radioimmunoassay using ganglioside-coated wells and assaying using a second antibody (rabbit anti-mouse IgM +IgG (Miles Biochemical, Elkhart, Ind.)) and $^{125}$I-labeled Protein A.

Monoclonal antibodies secreted by hybridomas thus isolated according to the method of the present invention can be produced in quantity by growing large batches of hybridoma cell cultures and purifying the antibody from the supernatant or by injecting mice with the hybridoma line to stimulate the production of ascites fluid. Both methods are well known in the art.

The hybridomas isolated according to the present invention can be grown in large batches in suspension culture, or more conveniently in a fiberglass container in which cells are packed and grown in high density, wherein antibodies can diffuse into the culture medium.

Methods of producing the monoclonal antibody in quantity according to the present invention are described in Young et al (supra).

The monoclonal antibodies can be purified by known methods, for example, by affinity separation using protein A or high pressure liquid chromatography on reverse phase alkylated silica gel or with a synthetic polystyrene gel filtration column.

According to the above described method, new hybridomas that produce new monoclonal antibodies directed to a variety of tumor-associated gangliosides, including human cancer-associated fucogangliosides can be made. These new antibodies have isotypes different from known antibodies showing similar binding specificity and many of the new antibodies have unique cross-reactivity. Further, this method differs over the previous method for immunizing with fucogangliosides in that, unexpectedly monoclonal antibodies having isotypes other than IgG$_3$ are obtained These include IgM and IgG$_1$.

Five preferred monoclonal antibodies that have been isolated according to the above method are SNH3, NKH1, NHK2, NKH3 and NKH4. The hybridomas that produce these monoclonal antibodies, designated hybridoma SNH3, NKH1, NKH2, NKH3 and NKH4, respectively, have been deposited with the American Type Culture Collection. Rockville, Md., and have ATCC Deposit Nos. HB 9941, HB 9942, HB 9943, HB 9944, and HB 9945, respectively.

Monoclonal antibody SNH3 according to the present invention is produced by hybridoma SNH3 and has the following important identifying characteristics:

(1) Isotype is IgM;
(2) Binds primarily to:
 (a) sialyl Le$^x$, and
 (b) sialyl difucosyl Le$^x$;
(3) Binds weakly, particularly on TLC immunostaining with pretreating by plastic coating material, to:
 (a) 2→3 sialylnorhexasoyl ceramide (VI$^3$-NeuAcnLc$_6$), and
 (b) extended Le$^x$ (VI$^3$NeuAcIII$^3$FucnLc$_6$)

This reactivity is distinct from that of many similar known antibodies, including FH6 and CSLEX.

Monoclonal antibody NKH1 according to the present invention is produced by hybridoma NKH1 and has the following important identifying characteristics:

(1) Isotype is IgG$_1$:
(2) Binds to sialyl 2→3 Le$^a$.

This reactivity is similar to that of known monoclonal antibodies N-19-9 and CSLEA. However, the isotype of monoclonal antibody NKHI is different from that of N-19-9 and CSLEA and thus its pharmacodynamic activity is expected to be different from that of N-19-9 and CSLEA.

Monoclonal antibody NKH2 according to the present invention is produced by hybridoma NKH2 and has the following important identifying characteristics:

(1) Isotype is IgM;
(2) Binds to:
 (a) sialyl 2→3 Le$^a$,
 (b) Le$^a$,
 (c) pentaosyl- and hexosylceramide carrying the La$^e$ epitope,
 (d) Le$^a$/Le$^x$ hybrid, and
 (e) bivalent Le$^a$ on lactoisooctaosylceramide.

Monoclonal antibody NKH2 is unique in its cross-reactivity with Le$^a$-containing structures.

Monoclonal antibodies NKH3 and NKH4 according to the present invention are produced by hybridomas NKH3 and NKH4, respectively, and have the following important identifying characteristics:

(1) Isotype is IgG$_1$;

munostaining with a plastic coated plate as is described in more detail in the working examples.

A summary of the isotypes of monoclonal antibodies SNH3, NKH1, NKH2, NKH3 and NKH4 according to the present invention and a detailed listing of the binding specificities of these monoclonal antibodies is set forth in Table I below.

TABLE I

Reactivity of tumor-associated gangliosides with monoclonal antibodies SNH3, NKH1, NKH2, NKH3 and NKH4

| | Structure | SNH3 (IgM) | NKH1 (IgG$_1$) | NKH2 (IgM) | NKH3 (IgG$_1$) | NKH4 (IgG$_1$) |
|---|---|---|---|---|---|---|
| 1. | NeuAcα2→3Galβ1→4GlcNAcβ1→3Galβ1→4Glcβ1→1Cer<br>　　　　　　　　　3<br>　　　　　　　　　↑<br>　　　　　　　　Fucα1 | + | − | − | − | − |
| 2. | NeuAcα2→3Galβ1→4GlcNAcβ1→3Galβ1→4GlcNAcβ1→3Galβ1→4Glcβ1→1Cer<br>　　　　　　　　　3　　　　　　　　　　3<br>　　　　　　　　　↑　　　　　　　　　　↑<br>　　　　　　　　Fucα1　　　　　　　　Fucα1 | + | − | − | − | − |
| 3. | NeuAcα2→3Galβ1→3GlcNAcβ1→3Galβ1→4Glcβ1→1Cer<br>　　　　　　　　　4<br>　　　　　　　　　↑<br>　　　　　　　　Fucα1 | − | + | + | + | + |
| 4. | NeuAcα2→3Galβ1→3GlcNAcβ1→3Galβ1→4Glcβ1→1Cer | − | − | − | + | + |
| 5. | Galβ1→3GlcNAcβ1→3Galβ1→4Glcβ1→1Cer<br>　　　　　　　　4<br>　　　　　　　　↑<br>　　　　　　　Fucα1 | − | − | + | − | − |
| 6. | Galβ1→4GlcNAcβ1→3Galβ1→4Glcβ1→1Cer<br>　　　　　　　3<br>　　　　　　　↑<br>　　　　　　Fucα1 | − | − | − | − | − |
| 7. | Galβ1→3GlcNAcβ1→3Galβ1→4GlcNAcβ1→3Galβ1→4Glcβ1→1Cer<br>　　　　4　　　　　　　　　　　3<br>　　　　↑　　　　　　　　　　　↑<br>　　　Fucα1　　　　　　　　　　Fucα1 | − | − | + | − | − |
| 8. | Fucα1<br>↓<br>3<br>Galβ1→3GlcNAcβ1<br>　　　　　　　＼<br>　　　　　　　　3<br>　　　　　　Galβ1→4GlcNAcβ1→3Galβ1→4Glcβ1→1Cer<br>　　　　　　　　6<br>　　　　　　　／<br>Galβ1→3GlcNAcβ1<br>　　3<br>　　↑<br>　Fucα1 | − | − | + | − | − |

(2) Bind to:

(a) sialyl 2→3 Le$^a$, and (b) sialyl 2→3 type 1 chain paragloboside, when tested with auxiliary lipids or by TLC immunostaining with plastic-coated plate.

Monoclonal antibodies NKH3 and NKH4 are similar to monoclonal antibody CA50 in apparent reactivity, but their isotype is different. Thus the pharmacodynamic activities of monoclonal antibodies NKH3 and NKH4 are expected to be different from the pharmacodynamic activity of monoclonal antibody CA50. Further, the reactivity of monoclonal antibodies NKH3 and NKH4 with sialyl 2→3 Le$^a$ is quite clear regardless of experimental conditions, whereas cross reactivity with sialyl type 1 chain paragloboside is unclear, unless the reactivity is tested with auxiliary lipids or by TLC im- The present invention also provides a passive immunization method for treatment of tumors containing gangliosides. The method comprises administering to a subject:

A pharmaceutically effective amount of an antibody produced by a method comprising:

(1) immunizing a host with tumor cells;

(2) boosting said host with a suspension comprising a mixture of tumor cell membrane and at least one purified lactonized tumor-associated ganglioside;

(3) boosting said host with an immunogen comprising a lactone of a tumor associated ganglioside adsorbed on or incorporated into a carrier;

(4) fusing immunized cells from said host with myeloma cells to form hybridoma cells;

(5) selecting hybridoma cells that produce antibody that binds to said ganglioside of step (3):

(6) culturing said selected hybridoma cells; and
(7) recovering said antibody.

The details of producing the antibody have been described above.

A pharmaceutically acceptable diluent can be employed in the immunization method of the present invention. The particular pharmaceutically acceptable diluent employed is not critical thereto. Examples of such diluents include physiological saline, Ringer's solution, vitamin cocktail and amino acid vitamin cocktail.

For administration of antibody to produce an antitumor effect in vivo, no carrier should be used. Purified antibodies are given intravenously without carrier material.

The pharmaceutically effective amount of the antibodies of the present invention to be administered will vary depending upon the age, weight, sex and species of the animal to be administered. Generally, the pharmaceutically effective amount is about 1.0 to 5.0 μg/100 g body weight of animal per one injection. Generally, from 5 to 10 injections of the antibodies are employed but the present invention is not limited thereto.

The particular antibody which will be administered will depend upon the particular ganglioside present in the tumor which is intended to be treated. Information as to the particular ganglioside present in the tumor can be obtained by a serum assay or biopsy assay for the various gangliosides. As used herein, "treatment" means both prevention of tumor formation and treatment of existing tumors.

The present invention also provides a method for detecting tumors containing gangliosides comprising:

(A) contacting a test sample with an antibody produced by a method comprising:

(1) immunizing a host with tumor cells;

(2) boosting said host with a suspension comprising a mixture of tumor cell membrane and at least one purified lactonized tumor-associated ganglioside;

(3) boosting said host with a lactone of a tumor associated ganglioside adsorbed on or incorporated into a carrier:

(4) fusing immunized cells from said host with myeloma cells to form hybridoma cells;

(5) selecting hybridoma cells that produce antibody that binds to said ganglioside of step (3);

(6) culturing said selected hybridoma cells; and (7) recovering said antibody and (B) assaying for specific binding of said antibody to antigen in said test sample.

In the method for detecting tumors containing gangliosides of the present invention, "test sample" means, for example, tissue biopsies, serum, ascites fluid and spinal fluid.

The method of producing the antibody has already been described in detail above.

Detection can occur either in vitro or in vivo. In vitro detection can be carried out using any of the well known in vitro immunological assays, such as those described by Young. W. W. et al. *J. Exp. Med.*, 150:1008–1019 (1979) and Kannagi, R. et al. *Cancer Res.*, 43:4997–5005 (1983). Further, in vivo detection can be carried out using any of the well known in vivo immunological assays, such as those described in Burchell, J. et al, *Int. J. Cancer*, 34:763–768 (1984); Epenetos, A. A. et al, *Lancet*, 2:999–1004 (1982); Chatal. J.-F. et al, *J. Nuclear Med.*, 25:307–314 (1984): Munz. Dil. et al. *J. Nuclear Med.*, 27:1739–1745 (1986); and Keenan. A.N. et al, *J. Nuclear Med.*, 26:531–537 (1985).

EXAMPLES

The following examples are provided for illustrative purposes only and are in no way intended to limit the scope of the present invention.

EXAMPLE 1

Production of SNH3, an IgM antibody defining sialyl $Le^x$ (structure 1, Table I)

Figure 1:
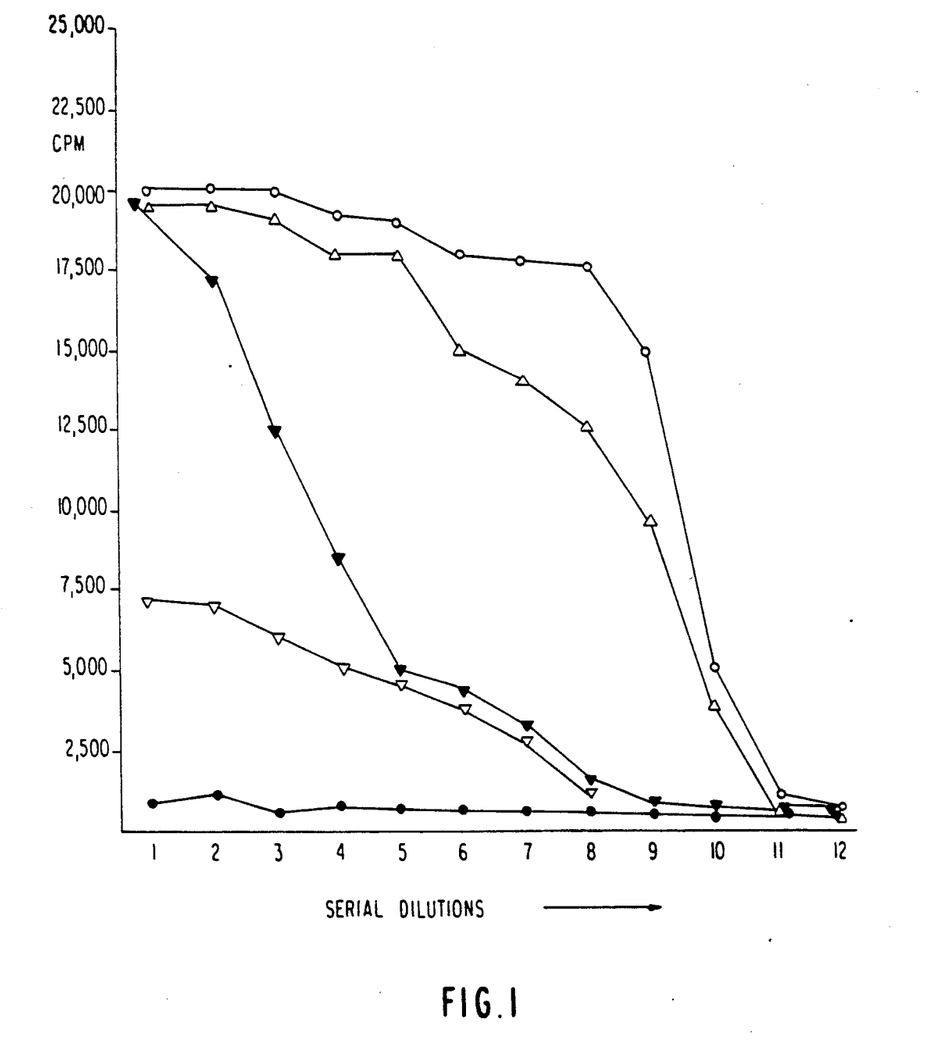
Figure 2A:
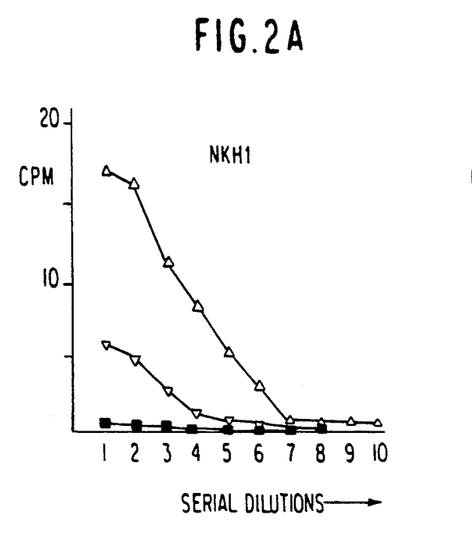
Figure 2B:
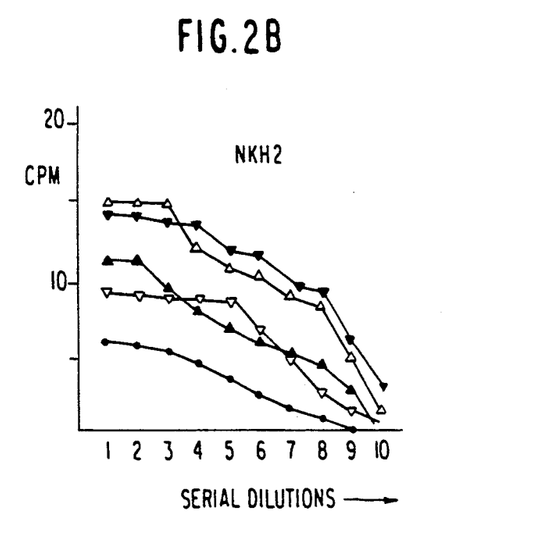
Figure 2C:
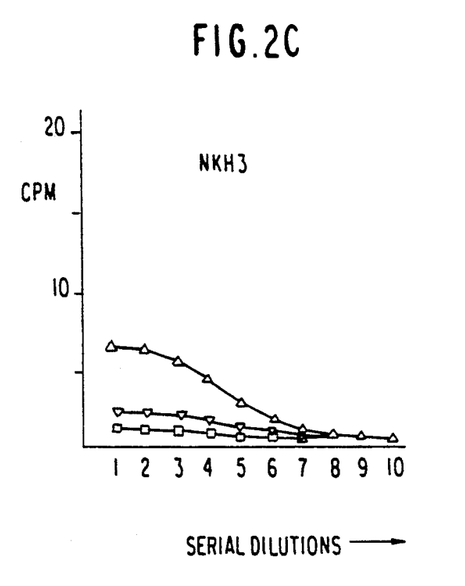
Figure 2D:
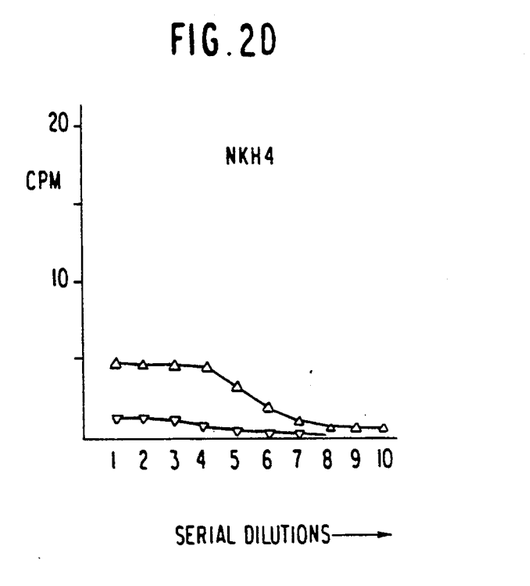
Figure 2E:
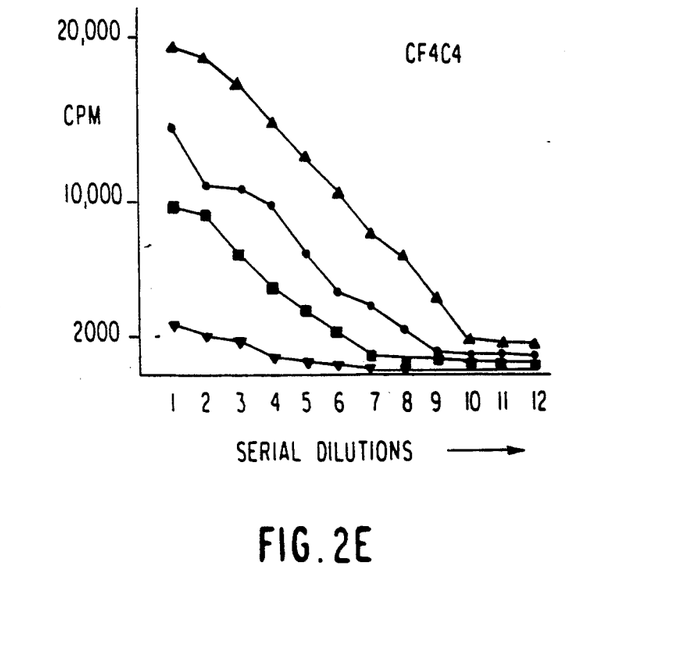
Figure 3A:
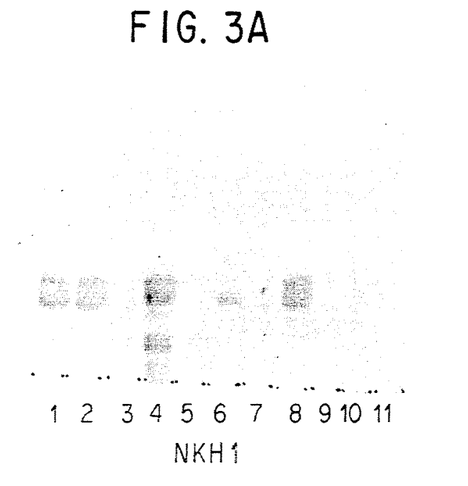
Figure 3B:
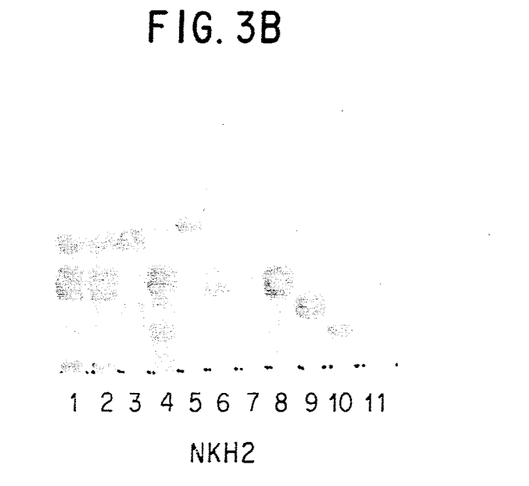
Figure 3C:
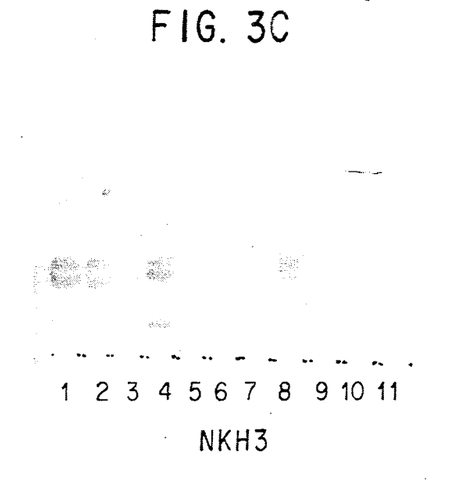
Figure 3D:
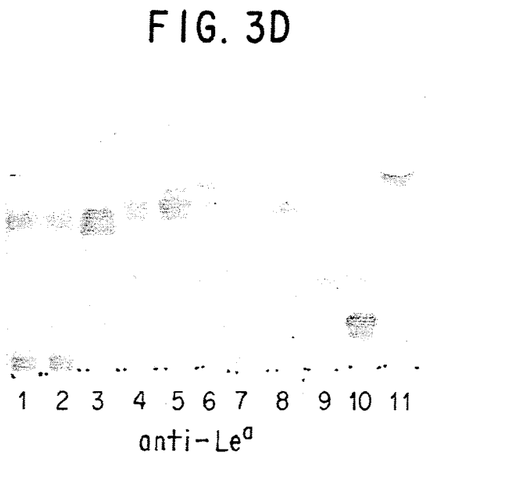

SNH3 antibody was established after immunization of mice with tumor cells and lactonized sialyl difucosyl $Le^x$ as follows. $10^6$ SW948 colonic cancer cells were injected intraperitoneally into Balb/c mice twice at weekly intervals (weeks 1 and 2). Next, $10^6$ human lung carcinoma PC9 cells were injected intraperitoneally at weeks 3 and 4. Finally, at week 5, lactonized sialyl difucosyl $Le^x$ adsorbed on *Salmonella minnesotae* was injected intravenously. Lactonization of sialyl difucosyl $Le^x$ ganglioside and adsorption on *S. minnesotae* followed by immunization were performed as previously described (Nores. G. A. et al, *J. Immunol.* 139:3171–3176 (1987)). Lactonization of sialyl difucosyl $Le^x$ was performed in glacial acetic acid (Nores, G. A. et al. *J. Immunol.* 139:3171–3176 (1987)) or treated with carbodiimide as recently described (Sonnino. S. et al. *Glycoconjugate J.* 2:343–354 (1985)). In the case of sialyl difucosyl $Le^x$ lactone antigen, 5 μg of the antigen was adsorbed on 40 μg of *S. minnesotae* suspended in 200 μl of phosphate buffered saline (PBS). and injected intravenously. Three days after the lactone injection, spleen cells were harvested and fused with mouse myeloma SP2 or NS1. Clones were screened by positive reactivity with the sialyl difucosyl $Le^x$ antigen (structure 2, Table I), and specificity of the antibody secreted by established hybridoma SNH3 was examined by TLC immunostaining and solid-phase radioimmunoassay according to known methods. Reactivity of the antibody SNH3 is shown in FIG. 1. Open circles, sialyl difucosyl $Le^x$ (structure 2, Table I) isolated from tumor. Open triangles, the same antigen synthesized enzymatically from sialyl 2→3 norhexaosylceramide. Closed, upside down triangles, sialyl $Le^x$ hexasaccharide ceramide isolated from tumor (structure 1, Table I). Open, upside down triangles, sialyl 2→3 norhexaosylceramide. Closed circles, GM3, 2→3 sialylparagloboside (SPG) ($IV^3NeuAcnLc_4$), 2→6 SPG ($IV^6NeuAcnLc_4$) 2→3 $Le^a$ (structure 3, Table I), sialyl 2→6 norhexaosylceramide ($VI^6NeuAcnLc_6$). Solid-phase radioimmunoassay was performed as previously described (Kannagi. R. et al. *Cancer Res.* 43:4997–5005 (1983)). The ordinate indicates the activity of protein A binding to primary and secondary antibody. The abscissa indicates antigen dilution, i.e., the first well (denoted as 1) contained 100 ng antigen, second well (denoted as 2) contained 50 ng antigen, etc.

The data in FIG. 1 shows that SNH3 antibody reacts preferentially with long-chain sialyl difucosyl $Le^x$, but also reacts reasonably well with short-chain sialyl $Le^x$ (i.e., sialyl $Le^x$ hexasaccharide ceramide). It is also weakly reactive with sialyl 2→3 lactonorhexaosylceramide ($VI^3NeuAcnLc_6$), and sialyl 2→3 lactonorhexaosylceramide having a fucosyl residue at the internal GlcNAc ($VI^3Neu AcIII^3FucnLc_6$). SNH3 is non-reactive with other related structures. This reactivity is distinctive from known reactivities of similar antibodies. i.e., it is different from that of FH6 (which does not react with short-chain sialyl Le$^x$ (IV$^3$NeuAcIII$^3$-FucnLc$_4$)) and CSLEX (which does not react with internally fucosylated sialyl 2→3 norhexaosyl or with sialy 2→3 norhexaosyl structures). This antibody is particularly useful as a diagnostic for serum assay of a large variety of human carcinomas.

EXAMPLE 2

Production of NKH1, 2, 3, and 4, defining sialyl 2→3 Le$^a$ (structure 3, Table I) and sialyl 2→3 type 1 chain (structure 4, Table I)

The isotype and specificity of each antibody are as follows:

| | |
|---|---|
| NKH1 | IgG$_1$; reacts specifically with sialyl 2→3 Le$^a$. |
| NKH2 | IgM; reacts primarily with sialyl 2→3 Le$^a$ but cross-reacts with Le$^a$. |
| NKH3 | IgG$_1$; reacts with both sialyl 2→3 Le$^a$ and SPG type 1 chain (similar to specificity of CA50). |
| NKH4 | IgG$_1$; reacts with both sialyl 2→3 Le$^a$ and SPG type 1 chain (very similar to NKH3; subtle difference can be seen in degree of cross-reactivity between the two ganglioside species). |

The procedures for preparation of the hybridomas were as follows:

a) Balb/c mice were immunized with 5×10$^6$ Colo205 whole cells intraperitoneally 3 times at intervals of 1 week.

b) Membrane fraction of Colo205 was prepared by known methods, suspended in 5% acetic acid, mixed with 3-5 μg purified gangliosides (sialyl 2→3 Le$^a$ and SPG type 1 chain) and lyophilized. This procedure induces lactonization and enrichment of membrane gangliosides. The material from lyophilization was suspended in PBS and injected intravenously at week 4.

c) 3-5 μg of purified lactonized ganglioside (sialyl 2→3 Le$^a$) prepared as described in Example 1, coated on 40 μg S. minnesotae in 200 μl saline by the method described in Example 1, was injected intravenously at week 5.

d) Spleen was harvested 3 days after the 5th injection and the splenocytes were fused with SP2 cells. Hybridomas were selected by specific reactivity with purified gangliosides sialyl 2→3 Le$^a$ and SPG type 1 chain as described in Example 1.

All hybridomas (NHK1, −2, −3, and −4) were prepared by this same procedure.

The reactivity of the NKH series antibodies by solid-phase radioimmunoassay is shown in FIG. 2, and their TLC immunostaining data is shown in FIG. 3.

The procedure used for solid-phase radioimmunoassay was as described previously (Kannagi. R. et al. *Cancer Res.* 43:4997-5005 (1983)). The antibody CF4C4 is a known anti-Le$^a$ antibody and was used to confirm that the Le$^a$ activity of various samples used for assay of NKH1, 2, 3 and 4 and to detect cross reactivity. The glycolipids having Le$^a$ determinants, such as structures 5, 7 and 8 in Table I, were positive with CF4C4, and structure 3 was negative with CF4C4 but positive with NKH2. The meanings of the symbols in FIG. 2 are as follows. Open triangles, sialyl 2→3 Le$^a$ purified from tumor (structure 3, Table I). Open, upside down triangles, the same antigen isolated from meconium (also contains disialyl Le$^a$). Closed squares, SPG type 1 chain. Closed triangles, Le$^a$ antigen (structure 5; Table I). Closed, upside down triangles, Le$^a$/Le$^x$ hybrid (structure 7, Table I). Closed circles, iso-Le$^a$ (structure 8, Table I). Open squares, synthetic sialyl 2→3 paraglobiside.

For the immunostaining patterns of various glycolipid samples with their respective antibodies shown in FIG. 3, glycolipids on each lane were developed in chloroform-methanol-water containing 0.01% CaCl$_2$ (55:30:10, v/v/v). The HPTLC plates were stained by a modified procedure of Magnani et al. (Magnani, J. L. et al *Anal. Biochem.* 109:399-402 (1980)). Lane 1: monosialoganglioside fraction of meconium: lane 2: monosialoganglioside fraction of meconium treated with sodium methoxide (in order to determine possible presence of gangliosides containing O-acetyl group): lane 3: upper neutral glycolipids of O erythrocytes; lane 4: monosialoganglioside fraction from human colonic cancer cell line Colo 205; lane 5: Le$^a$-active ceramide pentasaccharide (III$^4$FucLc$_4$Cer: structure 5, Table I); lane 6: sialyl 2→3 paragloboside type 1 chain isolated from meconium (structure 4, Table I): lane 7: sialyl 2→3 paragloboside type 1 chain synthesized from CMP-sialic acid and Lc$_4$Cer (type 1 chain paragloboside) (structure 4, Table I) lane 8: sialyl 2→3 Le$^a$ (IV$^3$-NeuAcIII$^4$FucLc$_4$Cer; structure 3, Table I): lane 9: Le$^a$ on Le$^x$ determinant (IV$^3$Galβ1→3[Fucα1→4]GlcNAc-III$^3$FucnLc$_4$Cer; structure 7, Table I); lane 10: Le$^a$ on branched lactoisooctaosylceramide (V$^3$FucIV$^6$-Galβ1→3-[Fucα1→3]GlcNAcnLc$_6$Cer; structure 8, Table I). The spot seen in lane 6 of FIG. 3B is due to contamination of 2→3 sialyl Le$^a$ and is not an indication of specificity.

The data in FIG. 2 and FIG. 3 shows the following:

(1) NKH1 is highly specific to sialyl 2→3 Le$^a$ and does not cross-react with 2→3 sialyl paragloboside (SPG) type 1 chain or paragloboside (PG) type 1 chain. This reactivity is similar to that of previously described antibodies such as N-19-9 (Magnani, J. L. et al *J. Biol. Chem.*, 257:14365-14369 (1982)) and CSLEA (Chia, D. et al, *Cancer Res.*, 45:435-437 (1985)). However, the isotype of NKH1 is different from that of N-19-9 and CSLEA.

(2) Antibody NKH2 is characterized by the way it reacts with both Le$^a$ and sialyl 2→3 Le$^a$. A weak reactivity was also demonstrated with PG type 1 chain. Such reactivity is novel; i.e., an antibody with such specificity has not been previously described.

(3) NKH3 and −4 react with both sialyl 2→3 Le$^a$ and sialyl 2→3 type 1 chain on TLC immunoblotting, although on solid-phase radioimmunoassay the reactivity with sialyl 2→3 Le$^a$ and SPG type 1 chain is weak.

In order to further test detailed specificity, type 1 chain analogues were synthesized enzymatically, as well as hybrid glycolipids having the structure Le$^a$ on Le$^x$ (structure 7, Table I) and bivalent Le$^x$ on lactoisooctaosylceramide (structure 8, Table I). The hybrid structure 7, Le$^a$ on Le$^x$; as well as bivalent Le$^a$, was reactive only with NKH2 antibody.

While the invention has been described in detail and with reference to specific embodiments thereof, it will be apparent to one skilled in the art that various changes and modifications can be made therein without departing from the spirit and scope thereof.

STATEMENT OF DEPOSIT

The hybridoma cell lines SNH3, NKH1, NKH2, NKH3 and NKH4 were deposited with the American Type Culture Collection, 12301 Parklawn Drive, Rockville Md., on Jan. 5, 1989 and have Deposit Nos. HB 9941, 9942, 9943, 9944 and 9945, respectively.

The deposits were made in accordance with the terms of the Budapest Treaty on the International Recognition of the Deposit of Microorganisms for the Purpose of Patent Procedure.

All restrictions to access will be irrevocably removed upon grant of a U.S. patent on the instant application.

What is claimed is:

1. A method of producing monoclonal antibodies that bind to tumor-associated gangliosides, the method comprising:

(1) immunizing a non-human host with tumor cells;
   (2) boosting said host with a suspension comprising a mixture of tumor cell membrane and at least one purified. lactonized tumor-associated ganglioside;
   (3) boosting said host with an immunogen comprising a lactonized tumor associated ganglioside adsorbed on or incorporated into a carrier;
   (4) fusing immunized cells from said host with myeloma cells to form hybridoma cells;
   (5) selecting hybridoma cells that produce antibody that binds to said ganglioside of step (3);
   (6) culturing said selected hybridoma cells; and
   (7) recovering said antibody.

2. The method of claim 1, wherein said tumor associated ganglioside of step (3) is sialyl difucosyl $Le^x$, sialyl $2\rightarrow3$ $Le^a$ isolated from a tumor or enzymatically synthesized, or sialyl $2\rightarrow3$ paragloboside.